United States Patent [19]
Wallingford

[11] Patent Number: 5,279,580
[45] Date of Patent: * Jan. 18, 1994

[54] HAND SYRINGE WITH SAFETY STORAGE FOR USED NEEDLE AND METHOD OF USE

[75] Inventor: Lawrence E. Wallingford, Wylie, Tex.

[73] Assignee: Retractable I., Inc., Garland, Tex.

[*] Notice: The portion of the term of this patent subsequent to Mar. 24, 2009 has been disclaimed.

[21] Appl. No.: 853,679

[22] Filed: Mar. 19, 1992

Related U.S. Application Data

[63] Continuation of Ser. No. 579,021, Sep. 7, 1990, Pat. No. 5,098,390.

[51] Int. Cl.⁵ .................................................. A61M 5/32
[52] U.S. Cl. .................................... 604/195; 604/243
[58] Field of Search ... 604/110, 195–197, 218, 240, 243

[56] References Cited

U.S. PATENT DOCUMENTS

| | | | |
|---|---|---|---|
| 4,507,117 | 3/1985 | Vining et al. | 604/196 |
| 4,675,005 | 6/1987 | DeLuccia | 604/110 |
| 4,874,382 | 10/1989 | Lindemann et al. | 604/195 |
| 4,919,652 | 4/1990 | Alter et al. | 604/110 |
| 4,921,486 | 5/1990 | Dechellis et al. | 604/110 |
| 4,931,040 | 6/1990 | Haber et al. | 604/110 |
| 4,957,490 | 9/1990 | Byrne et al. | 604/197 |
| 5,000,736 | 3/1991 | Kaufhold, Jr. et al. | 604/110 |
| 5,000,738 | 3/1991 | LaVallo et al. | 604/110 |
| 5,019,043 | 5/1991 | Pastir et al. | 604/110 |
| 5,047,016 | 9/1991 | Dolgin et al. | 604/110 |
| 5,098,390 | 3/1992 | Wallingford | 604/195 |
| 5,104,378 | 4/1992 | Haber et al. | 604/110 |

FOREIGN PATENT DOCUMENTS

| | | | |
|---|---|---|---|
| 0347742 | 12/1989 | European Pat. Off. | 604/110 |
| 9006146 | 6/1990 | PCT Int'l Appl. | 604/195 |

Primary Examiner—C. Fred Rosenbaum
Assistant Examiner—Adam J. Cermak
Attorney, Agent, or Firm—Baker & Botts

[57] ABSTRACT

An improved hand syringe has been provided which allows a used needle to be retracted completely into the body of the syringe, and stored there such that the spent needle cannot be used again. This improvement thereby provides safety from accidental infection to persons required to use hand syringes as well as persons required to dispose of these syringes.

2 Claims, 1 Drawing Sheet

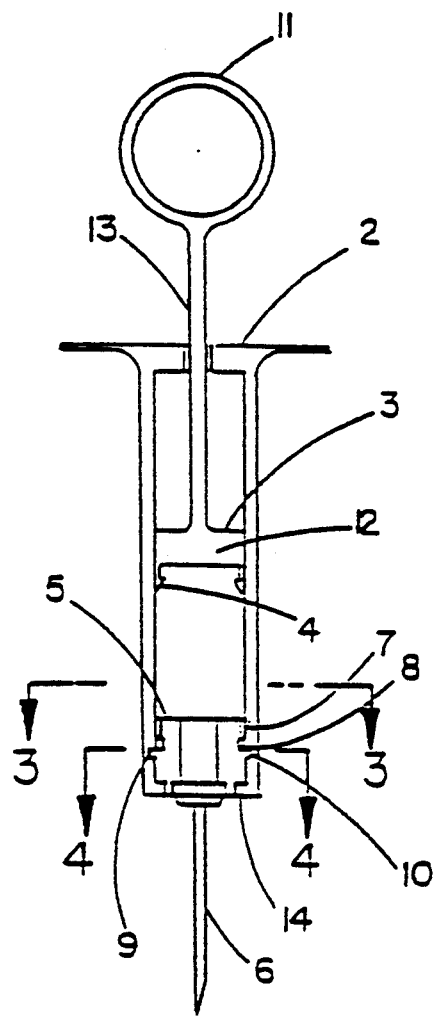
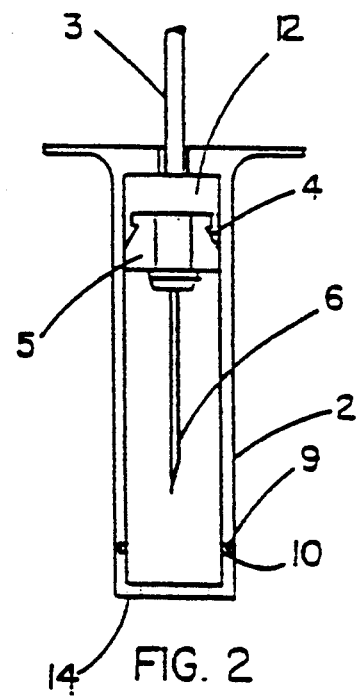
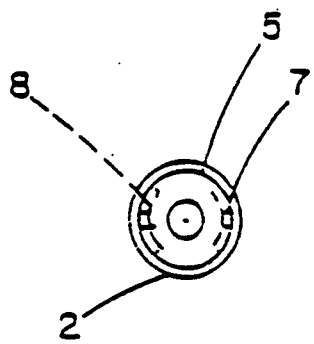
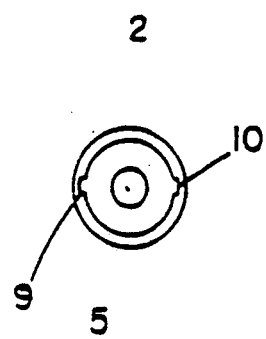
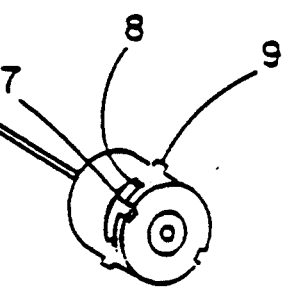
FIG. 1
FIG. 2
FIG. 3
FIG. 4
FIG. 5

HAND SYRINGE WITH SAFETY STORAGE FOR USED NEEDLE AND METHOD OF USE

RELATED APPLICATIONS

This application is a continuation application of U.S. application Ser. No. 07/579,021, filed Sep. 7, 1990 by Lawrence E. Wallingford entitled "Hand Syringe with Safety Storage for Used Needle and Method of Use," now U.S. Pat. No. 5,098,390 issued Mar. 24, 1992.

TECHNICAL FIELD OF THE INVENTION

The present invention relates in general to hand syringes, and more particularly to a hand syringe which allows a used needle to be retracted completely into the body of the syringe for storage.

BACKGROUND OF THE INVENTION

The prior art has taught means for enclosing a spent needle with a separate cover, breaking the used needle from the body of the syringe, spring actuation to push the needle back inside of the syringe body and several other approaches to eliminating secondary use of a hand syringe. Placing a cover over a used needle is not consistently done by the user, and breaking the needle is not a safe solution since users risk puncturing themselves while breaking the needle.

SUMMARY OF THE INVENTION

A primary object of the invention is to provide a convenient means to eliminate the secondary use of hand syringes thereby reducing the risk of transferring infection to otherwise healthy persons.

A further object of the invention is to provide a convenient storage means for a used hand syringe needle that will prevent service personnel from accidentally becoming infected from a previously used hand syringe.

A still further object of the invention is to provide a syringe structure that is simple and will be economical to produce using present injection molding art.

BRIEF DESCRIPTION OF THE DRAWINGS

Further features and advantages will become more apparent from the following and more particular description of the preferred embodiment of the invention, as illustrated in the accompanying drawings in which like reference characters generally refer to the same elements throughout the views, and in which:

FIG. 1 is a section view illustrating the several components of the instant invention with the injection needle positioned for use;

FIG. 2 is a section view picturing the injection needle in a stored position;

FIG. 3 is a section view taken along the lines 3—3 in FIG. 1;

FIG. 4 is a section view taken along the lines 4—4 in FIG. 1; and

FIG. 5 is a pictorial view of the needle head.

DETAILED DESCRIPTION OF THE INVENTION

Referring now to FIG. 1 in the drawings of reference, the instant invention 1 is shown to comprise a hollow cylindrical body 2 open on the distal end that houses a sliding plunger 3, a needle head 5 seated contiguous to lip 14, that is secured within, and at the distal end of hollow cylindrical body 2 by tab 9 seated in recess 10 that is formed in the inside diameter of body 2.

Plunger 3 is made with a thumb eye 11 on one end, and external to the syringe body, connected to piston 12 by means of shank 13. At least two locking tangs 4 extend downward from the bottom surface of piston 12.

The needle head 5 is formed with a standard syringe needle 6 of the appropriate size, at least two tang notches 7, and further, at least two circular slots 8 in the outside diameter of needle head 5.

The instant invention is used just as any other hand syringe. However, when the syringe needle 6 is stroked to completion, locking tangs 4 penetrate tang notches 7 allowing the lower face of piston 12 to come into intimate contact with the upper surface of needle head 5 at which time the plunger 3 is rotated several degrees in either clockwise or counter clockwise direction thereby causing the locking tangs 4 to be captured within slot 8. With the locking tangs 4 secured within slot 8, the plunger 3 is retracted causing the tabs 9 to tear away from the body of needle head 5 allowing needle head 5 to be retracted into the body 2 until the syringe needle 6 is encased by body 2, best seen in FIG. 2, and is now stored in a safe housing for disposal. The plunger shank 13 is now bent to one side of the body 2, thereby completely disabling the syringe for any further use.

FIG. 3 pictures a desired relationship of tang notch 7 with respect to the radial slots 8 in needle head 5.

FIG. 4 illustrates a suggested position for recess 10 with respect to tab 9.

FIG. 5 illustrates the relationship of tabs 9, tang notch 7, and radial slots 8 with respect to the needle head 5.

While the foregoing descriptions and drawings define the preferred embodiment of the instant invention, they do not preclude the many other means for accomplishing the same objectives that are within the scope and spirit of the instant invention.

What is claimed is:

1. An improved method of storing and disposing of used syringe needles after injection of a fluid into a diseased patient, thereby providing greater safety from accidental disease transmission to an individual responsible for making said injection, using a syringe having a hollow cylindrical body open on the distal end, a needle head including a locking tab slot for fixing the needle head at the distal end of said body, a syringe needle secured to said needle head, and a sliding plunger including tabs and movable within said hollow cylindrical body, comprising the steps of:

filling said hollow cylindrical body with fluid;

injecting the fluid into the patient by sliding said plunger toward the needle head;

continuing moving said plunger towards said needle head until the locking tabs are within said locking tab slots;

rotating said plunger and needle head until said locking tabs interlock with said locking tab slot;

withdrawing said plunger away from said needle head and causing said tabs on said needle head to be sheared; and continuing withdrawal of said sliding plunger until said needle head and syringe needle are completely encased within said hollow cylindrical body.

2. The method of claim 1 and further comprising:

bending said shank of said sliding plunger thereby securing said needle head and said syringe needle in a safe position within said hollow cylindrical body.

* * * * *